United States Patent [19]
Doi et al.

[11] Patent Number: 5,968,805
[45] Date of Patent: Oct. 19, 1999

[54] POLYESTER SYNTHASE AND A GENE CODING FOR THE SAME

[75] Inventors: Yoshiharu Doi; Toshiaki Fukui; Hiromi Matsusaki, all of Saitama, Japan

[73] Assignees: Japan Science and Technology Corporation; The Institute of Physical and Chemical Research, both of Saitama, Japan

[21] Appl. No.: 09/052,339

[22] Filed: Mar. 30, 1998

[30] Foreign Application Priority Data

Apr. 1, 1997 [JP] Japan .................................. 9-082965

[51] Int. Cl.$^6$ ............................... C12N 1/20; C12N 9/88; C12N 15/00; C07H 21/04
[52] U.S. Cl. ................... 435/252.3; 435/232; 435/320.1; 435/874; 435/135; 435/141; 435/142; 536/23.2; 536/23.7; 530/350; 530/300
[58] Field of Search ..................... 435/232, 183, 435/69.1, 252.3, 320.1, 874, 135, 141, 142; 536/23.2, 23.7; 530/350, 300

[56] References Cited

FOREIGN PATENT DOCUMENTS

| 9100917 | 1/1991 | WIPO . |
| WO 97/22711 | 6/1997 | WIPO . |

OTHER PUBLICATIONS

Timm, A. and Steinbuchel, A., "Cloning and molecular analysis of the poly(3–hydroxyalkanoic acid) gene locus of *Pseudomonas aeruginosa* PAO1" European Journal of Biochemistry, vol. 209n No. 1, Oct. 1992, pp. 15–30.

Huisman, G.W. et al., "Metabolism of poly(3–hydroxyalkanoates) (PHAs) by *Pseudomonas oleovorans*" The Journal of Biological Chemistry, vol. 266, No. 4, Feb. 5, 1991, pp. 2191–2198.

Timm, A. et al., "A general method for identification of polyhydroxyalkanoic acid synthase genes from pseudomonads belonging to the rRNA group I" Applied Microbiology and Biotechnology, vol. 40, No. 5, Jan. 1994, pp. 669–670.

Steinbuchel, A. et al., "Molecular basis for biosynthesis and accumulation of polyhydroxyalkanoic acids in bacteria" Fems Microbiology Reviews, vol. 103, No. 2–4, Dec. 1992, pp. 219–224.

Matsuzaki et al., Cloning of 2 polyester synthase genes possessed by *Pseudomonas* sp. 61–3,: Nippon Nogeikagaku Kaishi, vol. 71, Mar. 1997, p. 334.

*Primary Examiner*—Ponnathapura Achutamurthy
*Assistant Examiner*—Tekchand Saidha
*Attorney, Agent, or Firm*—John R. Wetherell, Jr.; Fish & Richardson P.C.

[57] ABSTRACT

The present invention relates to a polypeptide comprising the amino acid sequence of SEQ ID NO:1 or a sequence of SEQ ID NO:1 where in, one or more amino acids are deleted, replaced or added, and the polypeptide having polyester synthase activity. A polyester synthase gene comprising DNA coding for the above polypeptide; a recombinant vector comprising the gene; and a transformant transformed with the recombinant vector is also provided.

8 Claims, No Drawings

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
      (A) LENGTH: 559 amino acids
      (B) TYPE: amino acid
      (C) STRANDEDNESS:
      (D) TOPOLOGY: linear (ii) MOLECULE TYPE: protein (xi) SEQUENCE DESCRIPTION: SEQ ID NO: 1:

```
Met Ser Asn Lys Asn Ser Asp Asp Leu Asn Arg Gln Ala Ser Glu Asn
1               5                   10                  15

Thr Leu Gly Leu Asn Pro Val Ile Gly Leu Arg Gly Lys Asp Leu Leu
                20                  25                  30

Thr Ser Ala Arg Met Val Leu Thr Gln Ala Ile Lys Gln Pro Ile His
                35                  40                  45

Ser Val Lys His Val Ala His Phe Gly Ile Glu Leu Lys Asn Val Met
        50                  55                  60

Phe Gly Lys Ser Lys Leu Gln Pro Glu Ser Asp Asp Arg Arg Phe Asn
65                  70                  75                  80
```

-continued

Asp Pro Ala Trp Ser Gln Asn Pro Leu Tyr Lys Arg Tyr Leu Gln Thr
                    85                  90                  95

Tyr Leu Ala Trp Arg Lys Glu Leu His Asp Trp Ile Gly Asn Ser Lys
            100                 105                 110

Leu Ser Glu Gln Asp Ile Asn Arg Ala His Phe Val Ile Thr Leu Met
        115                 120                 125

Thr Glu Ala Met Ala Pro Thr Asn Ser Ala Ala Asn Pro Ala Ala Val
    130                 135                 140

Lys Arg Phe Phe Glu Thr Gly Gly Lys Ser Leu Leu Asp Gly Leu Thr
145                 150                 155                 160

His Leu Ala Lys Asp Leu Val Asn Asn Gly Gly Met Pro Ser Gln Val
                165                 170                 175

Asp Met Gly Ala Phe Glu Val Gly Lys Ser Leu Gly Thr Thr Glu Gly
            180                 185                 190

Ala Val Val Phe Arg Asn Asp Val Leu Glu Leu Ile Gln Tyr Arg Pro
        195                 200                 205

Thr Thr Glu Gln Val His Glu Arg Pro Leu Leu Val Pro Pro Gln
    210                 215                 220

Ile Asn Lys Phe Tyr Val Phe Asp Leu Ser Pro Asp Lys Ser Leu Ala
225                 230                 235                 240

Arg Phe Cys Leu Ser Asn Asn Gln Gln Thr Phe Ile Val Ser Trp Arg
                245                 250                 255

Asn Pro Thr Lys Ala Gln Arg Glu Trp Gly Leu Ser Thr Tyr Ile Asp
            260                 265                 270

Ala Leu Lys Glu Ala Val Asp Val Ser Ala Ile Thr Gly Ser Lys
        275                 280                 285

Asp Ile Asn Met Leu Gly Ala Cys Ser Gly Gly Ile Thr Cys Thr Ala
    290                 295                 300

Leu Leu Gly His Tyr Ala Ala Leu Gly Glu Lys Lys Val Asn Ala Leu
305                 310                 315                 320

Thr Leu Leu Val Ser Val Leu Asp Thr Thr Leu Asp Ser Gln Val Ala
                325                 330                 335

Leu Phe Val Asp Glu Lys Thr Leu Glu Ala Ala Lys Arg His Ser Tyr
            340                 345                 350

Gln Ala Gly Val Leu Glu Gly Arg Asp Met Ala Lys Val Phe Ala Trp
        355                 360                 365

Met Arg Pro Asn Asp Leu Ile Trp Asn Tyr Trp Val Asn Asn Tyr Leu
    370                 375                 380

Leu Gly Asn Glu Pro Pro Val Phe Asp Ile Leu Phe Trp Asn Asn Asp
385                 390                 395                 400

Thr Thr Arg Leu Pro Ala Ala Phe His Gly Asp Leu Ile Glu Met Phe
                405                 410                 415

Lys Asn Asn Pro Leu Val Arg Ala Asn Ala Leu Glu Val Ser Gly Thr
            420                 425                 430

Pro Ile Asp Leu Lys Gln Val Thr Ala Asp Ile Tyr Ser Leu Ala Gly
        435                 440                 445

Thr Asn Asp His Ile Thr Pro Trp Lys Ser Cys Tyr Lys Ser Ala Gln
    450                 455                 460

Leu Phe Gly Gly Lys Val Glu Phe Val Leu Ser Ser Gly His Ile
465                 470                 475                 480

Gln Ser Ile Leu Asn Pro Pro Gly Asn Pro Lys Ser Arg Tyr Met Thr
                485                 490                 495

Ser Thr Asp Met Pro Ala Thr Ala Asn Glu Trp Gln Glu Asn Ser Thr
            500                 505                 510

```
Lys His Thr Asp Ser Trp Trp Leu His Trp Gln Ala Trp Gln Ala Glu
    515                 520                 525

Arg Ser Gly Lys Leu Lys Lys Ser Pro Thr Ser Leu Gly Asn Lys Ala
    530                 535                 540

Tyr Pro Ser Gly Glu Ala Ala Pro Gly Thr Tyr Val His Glu Arg
545                 550                 555
```

(2) INFORMATION FOR SEQ ID NO: 2:

(i) SEQUENCE CHARACTERISTICS:
        (A) LENGTH: 1680 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 2:

```
ATGAGTAACA AGAATAGCGA TGACTTGAAT CGTCAAGCCT CGGAAAACAC CTTGGGCTT      60

AACCCTGTCA TCGGCCTGCG TGGAAAAGAT CTGCTGACTT CTGCCCGAAT GGTTTTAACC    120

CAAGCCATCA ACAACCCAT TCACAGCGTC AAGCACGTCG CGCATTTTGG CATCGAGCTG    180

AAGAACGTGA TGTTTGGCAA ATCGAAGCTG CAACCGGAAA GCGATGACCG TCGTTTCAAC    240

GACCCCGCCT GGAGTCAGAA CCCACTCTAC AAACGTTATC TACAAACCTA CCTGGCGTGG    300

CGCAAGGAAC TCCACGACTG GATCGGCAAC AGCAAACTGT CCGAACAGGA CATCAATCGC    360

GCTCACTTCG TGATCACCCT GATGACCGAA GCCATGGCCC CGACCAACAG TGCGGCCAAT    420

CCGGCGGCGG TCAAACGCTT CTTCGAAACC GGCGGTAAAA GCCTGCTCGA CGGCCTCACA    480

CATCTGGCCA AGGACCTGGT AAACAACGGC GGCATGCCGA GCCAGGTGGA CATGGGCGCT    540

TTCGAAGTCG GCAAGAGTCT GGGGACGACT GAAGGTGCAG TGGTTTTCCG CAACGACGTC    600

CTCGAATTGA TCCAGTACCG GCCGACCACC GAACAGGTGC ATGAGCGACC GCTGCTGGTG    660

GTCCCACCGC AGATCAACAA GTTTTATGTG TTTGACCTGA GCCGGATAA AAGCCTGGCG    720

CGCTTCTGCC TGAGCAACAA CCAGCAAACC TTTATCGTCA GCTGGCGCAA CCCGACCAAG    780

GCCCAGCGTG AGTGGGGTCT GTCGACTTAC ATCGATGCGC TCAAAGAAGC CGTCGACGTA    840

GTTTCCGCCA TCACCGGCAG CAAAGACATC AACATGCTCG GCGCCTGCTC CGGTGGCATT    900

ACCTGCACCG CGCTGCTGGG TCACTACGCC GCTCTCGGCG AGAAGAAGGT CAATGCCCTG    960

ACCCTTTTGG TCAGCGTGCT CGACACCACC CTCGACTCCC AGGTTGCACT GTTCGTCGAT   1020

GAGAAAACCC TGGAAGCTGC CAAGCGTCAC TCGTATCAGG CCGGCGTGCT GGAAGGCCGC   1080

GACATGGCCA AAGTCTTCGC CTGGATGCGC CCTAACGACC TGATCTGGAA CTACTGGGTC   1140

AACAACTACC TGCTGGGTAA CGAGCCACCG GTCTTCGACA TTCTTTTCTG GAACAACGAC   1200

ACCACCCGGT TGCCTGCTGC GTTCCACGGC GATCTGATCG AAATGTTCAA AAATAACCCA   1260

CTGGTGCGCG CCAATGCACT CGAAGTGAGC GGCACGCCGA TCGACCTCAA ACAGGTCACT   1320

GCCGACATCT ACTCCCTGGC CGGCACCAAC GATCACATCA CGCCCTGGAA GTCTTGCTAC   1380

AAGTCGGCGC AACTGTTCGG TGGCAAGGTC GAATTCGTGC TGTCCAGCAG TGGGCATATC   1440

CAGAGCATTC TGAACCCGCC GGGCAATCCG AAATACGTT ACATGACCAG CACCGACATG   1500

CCAGCCACCG CCAACGAGTG GCAAGAAAAC TCAACCAAGC ACACCGACTC CTGGTGGCTG   1560

CACTGGCAGG CCTGGCAGGC CGAGCGCTCG GGCAAACTGA AAAGTCCCC GACCAGCCTG   1620

GGCAACAAGG CCTATCCGTC AGGAGAAGCC GCGCCGGGCA CGTATGTGCA TGAACGTTAA   1680
```

(2) INFORMATION FOR SEQ ID NO: 3:

(i) SEQUENCE CHARACTERISTICS:
        (A) LENGTH: 1826 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 3:

```
CTGCAGTGCT CTCTGAACTA GAAAGCAACG TTGTGCAATT AACGGTCACC CGAGCAGTAG      60
TACCTGGCGG TTGCTGTGTG ACTACACAGC TGGTCCCGGT ACTCGTCTCA GGACAATGGA     120
GCGTCGTAGA TGAGTAACAA GAATAGCGAT GACTTGAATC GTCAAGCCTC GGAAAACACC     180
TTGGGGCTTA ACCCTGTCAT CGGCCTGCGT GGAAAAGATC TGCTGACTTC TGCCCGAATG     240
GTTTTAACCC AAGCCATCAA ACAACCCATT CACAGCGTCA AGCACGTCGC GCATTTTGGC     300
ATCGAGCTGA AGAACGTGAT GTTTGGCAAA TCGAAGCTGC AACCGGAAAG CGATGACCGT     360
CGTTTCAACG ACCCCGCCTG GAGTCAGAAC CCACTCTACA AACGTTATCT ACAAACCTAC     420
CTGGCGTGGC GCAAGGAACT CCACGACTGG ATCGGCAACA GCAAACTGTC CGAACAGGAC     480
ATCAATCGCG CTCACTTCGT GATCACCCTG ATGACCGAAG CCATGGCCCC GACCAACAGT     540
GCGGCCAATC CGGCGGCGGT CAAACGCTTC TTCGAAACCG GCGGTAAAAG CCTGCTCGAC     600
GGCCTCACAC ATCTGGCCAA GGACCTGGTA ACAACGGCG GCATGCCGAG CCAGGTGGAC      660
ATGGGCGCTT TCGAAGTCGG CAAGAGTCTG GGACGACTG AAGGTGCAGT GGTTTTCCGC      720
AACGACGTCC TCGAATTGAT CCAGTACCGG CCGACCACCG AACAGGTGCA TGAGCGACCG     780
CTGCTGGTGG TCCCACCGCA GATCAACAAG TTTTATGTGT TTGACCTGAG CCCGGATAAA     840
AGCCTGGCGC GCTTCTGCCT GAGCAACAAC CAGCAAACCT TTATCGTCAG CTGGCGCAAC     900
CCGACCAAGG CCCAGCGTGA GTGGGGTCTG TCGACTTACA TCGATGCGCT CAAAGAAGCC     960
GTCGACGTAG TTTCCGCCAT CACCGGCAGC AAAGACATCA ACATGCTCGG CGCCTGCTCC    1020
GGTGGCATTA CCTGCACCGC GCTGCTGGGT CACTACGCCG CTCTCGGCGA GAAGAAGGTC    1080
AATGCCCTGA CCCTTTTGGT CAGCGTGCTC GACACCACCC TCGACTCCCA GGTTGCACTG    1140
TTCGTCGATG AGAAAACCCT GGAAGCTGCC AAGCGTCACT CGTATCAGGC CGGCGTGCTG    1200
GAAGGCCGCG ACATGGCCAA AGTCTTCGCC TGGATGCGCC CTAACGACCT GATCTGGAAC    1260
TACTGGGTCA CAACTACCT GCTGGGTAAC GAGCCACCGG TCTTCGACAT TCTTTTCTGG     1320
AACAACGACA CCACCCGGTT GCCTGCTGCG TTCCACGGCG ATCTGATCGA AATGTTCAAA    1380
AATAACCCAC TGGTGCGCGC CAATGCACTC GAAGTGAGCG GCACGCCGAT CGACCTCAAA    1440
CAGGTCACTG CCGACATCTA CTCCCTGGCC GGCACCAACG ATCACATCAC GCCCTGGAAG    1500
TCTTGCTACA AGTCGGCGCA ACTGTTCGGT GGCAAGGTCG AATTCGTGCT GTCCAGCAGT    1560
GGGCATATCC AGAGCATTCT GAACCCGCCG GGCAATCCGA AATCACGTTA CATGACCAGC    1620
ACCGACATGC CAGCCACCGC CAACGAGTGG CAAGAAAACT CAACCAAGCA CACCGACTCC    1680
TGGTGGCTGC ACTGGCAGGC CTGGCAGGCC GAGCGCTCGG GCAAACTGAA AAAGTCCCCG    1740
ACCAGCCTGG GCAACAAGGC CTATCCGTCA GGAGAAGCCG CGCCGGGCAC GTATGTGCAT    1800
GAACGTTAAG TTGTAGGCAG TCTAGA                                        1826
```

(2) INFORMATION FOR SEQ ID NO: 4:

(i) SEQUENCE CHARACTERISTICS:
        (A) LENGTH: 24 base pairs
        (B) TYPE: nucleic acid

```
            (C) STRANDEDNESS: single
            (D) TOPOLOGY: linear (ii) MOLECULE TYPE: other nucleic acid
            (A) DESCRIPTION:   /desc = "synthetic DNA"

(xi) SEQUENCE DESCRIPTION: SEQ ID NO: 4:

CCSCAGATCA ACAAGTTYTA SGAC                                              24
```

POLYESTER SYNTHASE AND A GENE CODING FOR THE SAME

FIELD OF THE INVENTION

The present invention relates to polyester synthase, a gene coding for the enzyme, a recombinant vector containing the gene, a transformant transformed with the vector, and a process for producing polyester synthase by use of the transformant.

BACKGROUND OF THE INVENTION

Polyesters (e.g. poly-3-hydroxyalkanoic acid) biosynthesized by microorganisms are biodegradable plastics with thermoplasticity ranging widely from rigid matter to viscoelastic rubber.

Poly-3-hydroxybutanoic acid (P(3HB)) is a typical polyester consisting of C4 monomer units, but it is a rigid and brittle polymeric material, so its application is limited. Accordingly, various polyesters such as P(3HB-co-3HV) having (P(3HB)) copolymerized with a C5 monomer unit (3HV) by adding propionic acid etc. to the medium have been prepared and examined to alter the physical properties of the polyester. On the other hand, polyesters consisting of at least C6 monomer units are soft polymeric materials having plasticity.

Polyester-synthesizing microorganisms are roughly divided into 2 groups, that is, those synthesizing polyesters with C3–5 monomer units and those synthesizing polyesters with C6–14 monomer units. The former microorganisms possess a polyester synthase using C3–5 monomer units as the substrate, while the latter microorganisms possess a polyester synthase using C6–14 monomer units as the substrate. Therefore, polyesters with different properties are synthesized by the respective microorganisms.

However, the respective polyesters from such known microorganisms are different in substrate specificity, so with one kind of enzyme given, polyesters (copolymers) having various monomer unit compositions adapted to the object of use are difficult to synthesize.

SUMMARY OF THE INVENTION

The object of the present invention is to provide a polyester synthase with monomer units having a wide range of carbon atoms as the substrate, a gene coding for the enzyme, a recombinant vector containing the gene, a transformant transformed with the vector, and a process for producing the polyester synthase by use of the transformant.

As a result of their eager research, the present inventors succeeded in cloning a polyester synthase gene from a microorganism belonging to the genus Pseudomonas isolated from soil, to arrive at the completion of the present invention.

That is, the present invention is a polypeptide comprising the amino acid sequence of SEQ ID NO:1 or a sequence where in said amino acid sequence, one or more amino acids are deleted, replaced or added, said polypeptide having polyester synthase activity.

Further, the present invention is a polyester synthase gene comprising DNA coding for said polypeptide. The DNA coding for the protein with polyester synthase activity includes e.g. that of SEQ ID NO:2.

Further, the present invention is a polyester synthase gene comprising the nucleotide sequence of SEQ ID NO:3.

Further, the present invention is a recombinant vector comprising the polyester synthase gene.

Further, the present invention is a transformant transformed with said recombinant vector.

Further, the present invention is a process for producing polyester synthase wherein said transformant is cultured in a medium and polyester synthase is recovered from the resulting culture.

DETAILED DESCRIPTION OF THE INVENTION

Hereinafter, the present invention is described in detail.
(1) Cloning of the Polyester Synthase Gene The polyester synthase gene of the present invention is separated from a microorganism belonging to the genus Pseudomonas.

First, genomic DNA is isolated from a strain having the polyester synthase gene. Such a strain includes e.g. Pseudomonas sp. Any known methods can be used for preparation of genomic DNA. For example, Pseudomonas sp. is cultured in a bouillon medium and then its genomic DNA is prepared by the hexadecyl trimethyl ammonium bromide method (Current Protocols in Molecular Biology, vol. 1, page 2.4.3., John Wiley & Sons Inc., 1994).

The DNA obtained in this manner is partially digested with a suitable restriction enzyme (e.g. Sau3AI, BamHI, BglII etc.). It is then ligated into a vector dephosphorylated by treatment with alkaline phosphatase after cleavage with a restriction enzyme (e.g. BamHI, BglII etc.) to prepare a library.

Phage or plasmid capable of autonomously replicating in host microorganisms is used as the vector. The phage vector includes e.g. EMBL3, M13, λgt11 etc., and the plasmid vector includes e.g. pBR322, pUC18, and pBluescript II (Stratagene). Vectors capable of autonomously replicating in 2 or more host cells such as E. coli and Bacillus brevis, as well as various shuttle vectors, can also be used. Such vectors are also cleaved with said restriction enzymes so that their fragment can be obtained.

Conventional DNA ligase is used to ligate the resulting DNA fragment into the vector fragment. The DNA fragment and the vector fragment are annealed and then ligated to produce a recombinant vector.

To introduce the recombinant vector into a host microorganism, any known methods can be used. For example, if the host microorganism is E. coli, the calcium chloride method (Lederberg, E. M. et al., J. Bacteriol. 119, 1072 (1974)) and the electroporation method (Current Protocols in Molecular Biology, vol. 1, page 1.8.4 (1994)) can be used. If phage DNA is used, the in vitro packaging method (Current Protocols in Molecular Biology, vol. 1, page 5.7.1 (1994)) etc. can be adopted. In the present invention, an in vitro packaging kit (Gigapack II, produced by Stratagene etc.) may be used.

To obtain a DNA fragment containing the polyester synthase gene derived from Pseudomonas sp., a probe is then prepared. The amino acid sequences of some polyester synthases have already been known (Peoples, O. P. and Sinskey, A. J., J. Biol. Chem., 264, 15293 (1989); Huisman, G. W. et al., J. Biol. Chem., 266, 2191 (1991); Pieper, U. et al., FEMS Microbiol. Lett., 96, 73 (1992); Timm, A. and Steinbuchel, A., Eur. J. Biochem., 209, 15 (1992), etc.) . Well-conserved regions are selected from these amino acid sequences, and nucleotide sequences coding for them are estimated to design oligonucleotides. Examples of such oligonucleotides include, but are not limited to, the sequence 5'-CC(G/C)CAGATCAACAAGTT(C/T)TA(C/G)GAC-3' (SEQ ID NO:4) reported by Timm, A. and Steinbuchel, A., Eur. J. Biochem., 209, 15 (1992).

Then, this synthetic oligonucleotide is labeled with a suitable reagent and used for colony hybridization of the above genomic DNA library (Current Protocols in Molecular Biology, vol. 1, page 6.0.3 (1994)).

The E. coli is screened by colony hybridization, and a plasmid is recovered from it using the alkaline method (Current Protocols in Molecular Biology, vol. 1, page 1.6.1 (1994)), whereby a DNA fragment containing the polyester synthase gene is obtained. The nucleotide sequence of this DNA fragment can be determined in e.g. an automatic nucleotide sequence analyzer such as 373A DNA sequencer (Applied Biosystems) using a known method such as the Sanger method (Molecular Cloning, vol. 2, page 13.3 (1989)).

After the nucleotide sequence was determined by the means described above, the gene of the present invention can be obtained by chemical synthesis or the PCR technique using genomic DNA as a template, or by hybridization using a DNA fragment having said nucleotide sequence as a probe.

(2) Preparation of Transformant

The transformant of the present invention is obtained by introducing the recombinant vector of the present invention into a host compatible with the expression vector used in constructing said recombinant vector.

The host is not particularly limited insofar as it can express the target gene. Examples are bacteria such as microorganisms belonging to the genus Alcaligenes, microorganisms belonging to the genus Bacillus, bacteria such as E. coli, yeasts such as the genera Saccharomyces, Candida etc., and animal cells such as COS cells, CHO cells etc.

If microorganisms belonging to the genus Alcaligenes or bacteria such as E. coli are used as the host, the recombinant DNA of the present invention is preferably constituted such that it contains a promoter, the DNA of the present invention, and a transcription termination sequence so as to be capable of autonomous replication in the host. The expression vector includes pLA2917 (ATCC 37355) containing replication origin RK2 and pJRD215 (ATCC 37533) containing replication origin RSF1010, which are replicated and maintained in a broad range of hosts.

The promoter may be any one if it can be expressed in the host. Examples are promoters derived from E. coli, phage etc., such as trp promoter, lac promoter, PL promoter, PR promoter and T7 promoter. The method of introducing the recombinant DNA into bacteria includes e.g. a method using calcium ions (Current Protocols in Molecular Biology, vol. 1, page 1.8.1 (1994)) and the electroporation method (Current Protocols in Molecular Biology, vol. 1, page 1.8.4 (1994)).

If yeast is used as the host, expression vectors such as YEp13, YCp50 etc. are used. The promoter includes e.g. gal 1 promoter, gal 10 promoter etc. To method of introducing the recombinant DNA into yeast includes e.g. the electroporation method (Methods. Enzymol., 194, 182–187 (1990)), the spheroplast method (Proc. Natl. Acad. Sci. USA, 84, 1929–1333 (1978)), the lithium acetate method (J. Bacteriol., 153, 163–168 (1983)) etc.

If animal cells are used as the host, expression vectors such as pcDNAI, pcDNAI/Amp (produced by Invitrogene) etc. are used. The method of introducing the recombinant DNA into animal cells includes e.g. the electroporation method, potassium phosphate method etc.

(3) Production of Polyester Synthase

Production of the Polyester Synthase of the present invention is carried out by culturing the transformant of the present invention in a medium, forming and accumulating the polyester synthase of the present invention in the culture (the cultured microorganism or the culture supernatant) and recovering the polyester synthase from the culture.

A conventional method used for culturing the host is also used to culture the transformant of the present invention.

The medium for the transformant prepared from bacteria such as E. coli etc. as the host includes complete medium or synthetic medium, e.g. LB medium, M9 medium etc. The transformant is aerobically cultured at a temperature ranging from 25 to 37° C. for 12 to 48 hours so that the polyester synthase is accumulated in the microorganism and then recovered.

The carbon source is essential for the growth of the microorganism and includes e.g. carbohydrates such as glucose, fructose, sucrose, maltose etc.

The nitrogen source includes e.g. ammonia, ammonium salts such as ammonium chloride, ammonium sulfate, ammonium phosphate etc., peptone, meat extract, yeast extract, corn steep liquor etc. The inorganic matter includes e.g. monopotassium phosphate, dipotassium phosphate, magnesium phosphate, magnesium sulfate, sodium chloride etc.

Culture is carried out usually under aerobic conditions with shaking at 25 to 37° C. for more than 2 hours after expression is induced. During culture, antibiotics such as ampicillin, kanamycin, ampicillin, tetracycline etc. may be added to the culture.

To culture the microorganism transformed with the expression vector using an inducible promoter, its inducer can also be added to the medium. For example, isopropyl-β-D-thiogalactopyranoside (IPTG), indoleacrylic acid (IAA) etc. can be added to the medium.

To culture the transformant from animal cells as the host, use is made of a medium such as RPMI-1640 or DMEM which may be supplemented with fetal bovine serum. Culture is carried out usually in 5% $CO_2$ at 30 to 37° C. for 1 to 7 days. During culture, antibiotics such as kanamycin, penicillin etc. may be added to the medium.

Purification of the polyester synthase can be performed by recovering the resulting culture by centrifugation (after disruption in the case of cells) and subjecting it to affinity chromatography, cation or anion exchange chromatography or gel filtration or to a suitable combination thereof.

Whether the resulting purified substance is the desired enzyme is confirmed by conventional methods such as SDS polyacrylamide gel electrophoresis, Western blotting etc.

Examples

Hereinafter, the present invention is described in more detail with reference to the Examples which however are not intended to limit the scope of the present invention.

(1) Cloning of the Polyester Synthase Gene from Pseudomonas sp.

First, a genomic DNA library of Pseudomonas sp. was prepared.

Pseudomonas sp. JCM 10015 was cultured overnight in 100 ml bouillon medium (1% meat extract, 1% peptone, 0.5% sodium chloride, pH 7.2) at 30° C. and then genomic DNA was obtained from the microorganism using the hexadecyl trimethyl ammonium bromide method (Current Protocols in Molecular Biology, vol. 1, page 2.4.3 (1994), John Wiley & Sons Inc.).

The resulting genomic DNA was partially digested with restriction enzyme Sau3AI. The vector plasmid used was cosmid vector pLA2917 (ATCC 37355). This plasmid was cleaved with restriction enzyme BglII and dephosphorylated (Molecular Cloning, vol. 1, page 5.7.2 (1989), Cold Spring Harbor Laboratory) and then ligated into the partially digested genomic DNA fragment by use of DNA ligase.

E. coli S17-1 was transformed with this ligated DNA fragment by the in vitro packaging method (Current Protocols in Molecular Biology, vol. 1, page 5.7.2 (1994)) whereby a genomic DNA library from Pseudomonas sp. was obtained.

To obtain a DNA fragment containing the polyester synthase gene from Pseudomonas sp., a probe was then prepared. An oligonucleotide consisting of the sequence 5'-CC(G/C)CAGATCAACAAGTT(C/T)TA(C/G)GAC-3' (SEQ ID NO:4) reported by Timm, A. and Steinbuchel, A., Eur. J. Biochem., 209, 15 (1992) was synthesized. This oligonucleotide was labeled with digoxigenin using a DIG DNA labeling kit (Boehringer Mannheim) and used as a probe.

Using the probe thus obtained, E. coli carrying a plasmid containing the polyester synthase gene was isolated by colony hybridization from the genomic DNA library from Pseudomonas sp.

When Alcaligenes eutrophus PHB-4 (DSM541) and Pseudomonas putida GPp104 (both of which are strains deficient in an ability to produce polyester) were transformed by the conjugation transfer method with the plasmid containing the polyester synthase gene, both the strains had a reverse ability to produce polyester and showed complementarity.

By recovering the plasmid from the E. coli, a DNA fragment containing the polyester synthase gene was obtained.

The nucleotide sequence of a PstI-XbaI fragment from this fragment was determined by the Sanger method.

As a result, the nucleotide sequence of the 1.8 kbp fragment shown in SEQ ID NO:3 was determined.

By further examining homology to this nucleotide sequence, the polyester synthase gene containing the nucleotide sequence (1680 bp) of SEQ ID NO:2 could be identified in this 1.8 kbp nucleotide sequence. The amino acid sequence encoded by SEQ ID NO:2 is shown in SEQ ID NO:1.

It should be understood that insofar as a protein containing the amino acid sequence of SEQ ID NO:1 or a sequence where in said amino acid sequence, one or more amino acids are deleted, replaced or added has polyester synthase activity, the gene (SEQ ID NO:2 or 3) containing DNA coding for said protein falls under the scope of the polyester synthase gene of the present invention.

Mutations such as deletion, replacement, addition etc. can be induced in the amino acid sequence or nucleotide sequence by the known site-direct mutagenesis method (e.g. Transfomer™ Site-Directed Mutagenesis Kit available from Toyobo).

(2) Preparation of E. coli transformant

The 1.8 kb PstI-XbaI fragment containing the polyester synthase gene was ligated into the XbaI, PstI site of plasmid vector pBluescript II KS+. The resulting recombinant vector was transformed by the calcium chloride method into Escherichia coli DH5α. The resulting transformant was designated Escherichia coli PX18. By extracting the plasmid from this transformant, the 1.8 kb PstI-XbaI fragment containing the polyester synthase gene can be easily obtained. Escherichia coli PX18 has been deposited as FERM BP-6297 with the National Institute of Bioscience and Human-Technology, Agency of Industrial Science and Technology, Japan.

According to the present invention, there are provided a gene coding for polyester synthase, a recombinant vector containing the gene, and a transformant transformed with the vector. The gene of the present invention codes for a polyester synthase using monomers having a wide range of carbon atoms as the substrate, so it is useful in preparing copolymer polyesters having various physical properties.

What is claimed is:

1. An isolated polynucleotide encoding a polypeptide having a sequence as set forth in SEQ ID NO:1.

2. An isolated polynucleotide selected from the group consisting of:

a) SEQ ID NO:2;

b) SEQ ID NO:2, wherein T is U; and c) nucleic acid sequences complementary to a) or b).

3. An isolated polynucleotide selected from the group consisting of:

a) SEQ ID NO:3;

b) SEQ ID NO:3, wherein T is U; and c) nucleic acid sequences complementary to a) or b).

4. A vector containing a polynucleotide of claim 1, 2 or 3.

5. The vector of claim 4, wherein the vector is a viral vector.

6. The vector of claim 4, wherein the vector is a plasmid.

7. A host cell containing a vector of claim 4.

8. The host cell of claim 7, cultured under conditions which allow expression of the polynucleotide.

* * * * *